United States Patent [19]

Messing et al.

[11] 4,153,510
[45] May 8, 1979

[54] HIGH SURFACE LOW VOLUME BIOMASS COMPOSITE

[75] Inventors: Ralph A. Messing, Horseheads; Robert A. Oppermann, Painted Post, both of N.Y.

[73] Assignee: Corning Glass Works, Corning, N.Y.

[21] Appl. No.: 833,278

[22] Filed: Sep. 14, 1977

[51] Int. Cl.$^2$ .............................................. C12B 1/00
[52] U.S. Cl. ...................................... 195/59; 195/53; 195/54; 195/56
[58] Field of Search ............ 195/116, 63, 68, DIG. 11, 195/52, 53, 54, 57, 59, 60, 28 R, 115

[56] References Cited

U.S. PATENT DOCUMENTS

| | | | |
|---|---|---|---|
| 3,616,246 | 10/1971 | Cherry | 195/81 |
| 3,850,751 | 11/1974 | Messing | 195/63 |
| 3,875,008 | 4/1975 | Yoshino et al. | 195/63 |
| 3,892,580 | 7/1975 | Messing | 106/41 |
| 3,983,000 | 9/1976 | Messing et al. | 195/63 |
| 4,001,085 | 1/1977 | Keyes | 195/68 |
| 4,071,409 | 1/1978 | Messing et al. | 195/63 |

FOREIGN PATENT DOCUMENTS 979547  12/1975  Canada ..................................... 195/116

OTHER PUBLICATIONS

Methods in Enzymology, vol. 44, pp. 148-159 (1976).

Primary Examiner—Lionel M. Shapiro
Attorney, Agent, or Firm—William E. Maycock; Clinton S. Janes, Jr.; Clarence R. Patty, Jr.

[57] ABSTRACT

Immobilized microbe composite comprising a porous, high surface area inorganic support having a controlled population of microbes bonded to the internal surfaces of the pores, the support being water insoluble, non-toxic to the microbes, and having a controlled porosity such that at least 70% of the pores, on a pore size distribution basis, have a pore diameter at least as large as the smallest major dimension of the microbes but less than about five times the largest major dimension of the microbes. The composites are especially useful in situations requiring a high biomass surface within a relatively small volume.

16 Claims, 7 Drawing Figures

HIGH SURFACE LOW VOLUME BIOMASS COMPOSITE

BACKGROUND OF THE INVENTION

1. Field

This disclosure is concerned generally with the attachment and growth of microbes on inorganic surfaces. Specifically, the disclosure is concerned with providing a porous inorganic support for the immobilization of a controlled population of microbes.

2. Prior Art

The preparation and use of composites consisting of microbes (bacteria, yeast cells, etc.) fixed on the surfaces of support materials is very old and well known. Typically, a film or slime of microbes is allowed to grow over the surfaces of the support. The resultant film provides a biomass which, depending on the microbes involved, can be used in various practical applications. For example, one of the earlier trickling filter fermentation systems involved using wood shavings or other supports as a packing material which was placed in a container such as a barrel. A liquid raw material was allowed to trickle through the packing and, in some cases, air was allowed to pass upward through the packing. As the liquid was circulated with a simple pump, a film of microbes would form on the surfaces of the packing, thereby resulting in a relatively large accumulation of useful biomass which, depending on the type of microbial film (anaerobic or aerobic conditions), could be used to ferment sugars to alcohol (anaerobic) or convert alcohol to acids (aerobic). The latter process could be used to make vinegar. Early trickling filter systems of that type were commonly referred to as Schuetzenbach generators.

Numerous variations of that type of fermenting system are well known. See, for example, U.S. Pat. No. 454,586 to Bachmann which describes a fermenting vat for the fermentation of sugar solutions to a variety of products. The system consists of a flow-through vat containing a porous packing material. In that patent it was pointed out that the fermentation "germs" of a liquid substrate appeared to multiply more rapidly within the pores and on the surfaces of the packing than when the "germs" were freely floating in the liquid.

Other microbe support systems describing the use of high surface area microbe supports are shown in U.S. Pat. No. 2,440,545 (saw dust, alfalfa chops, cut straw, glass beads, stone grit, etc.); U.S. Pat. No. 3,709,364 (use of sand particles for sewage treatment); U.S. Pat. No. 3,402,103 (series of baffles in a flow through reactor upon which bacterial films are formed); and Indian Pat. No. 43542 (use of porous particles of pumice as supports for yeast cells). From a sampling of the prior art, it is quite clear that others have long appreciated certain advantages of using porous, high surface area inorganic materials as supports for microbial films.

While it can be readily appreciated that there exists a relationship between the porosity of a given support material and the useable surface area that the material provides in a given application, we have now found, quite surprisingly, that in the case of porous supports for microbes, there exists a range of pore sizes which, vis-a-vis the microbe size, provides an extremely large surface but low volume for a high biomass concentration. Details of our findings and the immobilized microbe composites resulting therefrom are described in detail herein.

SUMMARY OF THE INVENTION

Our immobilized microbe composites comprise a porous, high surface area inorganic support material having a controlled population of microbes bonded to the internal surfaces of the pores, the support being water-insoluble, non-toxic to the microbes, and having a controlled porosity such that at least 70% of the pores, on a pore size distribution basis, have a pore diameter at least as large as the smallest major dimension of the microbes but less than about five times the largest major dimension of the microbes. Such composites provide a relatively large biomass surface within a relatively small volume. In preferred embodiments, the population of microbes comprises a single species of bacteria and the inorganic support comprises material in which pore size distribution can be readily and economically controlled (e.g. amorphous or glass materials such as fritted glasses, or crystalline materials such as cordierite-like materials, etc.), and the average pore diameter of the inorganic support, for the majority of composite combinations, ranges from about 0.8 to about 220 microns.

SPECIFIC EMBODIMENTS

The importance of accumulating very large biomass surfaces in a limited reaction volume can be appreciated by considering some of the practical applications of immobilized microbes in general. It is well known, for example, that the mere multiplication of microbial cells can be a basis for the rapid generation of proteinaceous matter. By providing optimum conditions favoring microbial cell reproduction on a continuous basis, the accumulated cells can, under some conditions, be processed for their protein value. This is the basis for so-called single cell protein technology (SCP).

Although SCP production is presently available on a continuous (cf. batch) basis using systems known as chemostats or turbidostats, it can be appreciated that, except for wall effects, the bulk of the reproducing cells are merely suspended in a nutrient medium. Although there are certain advantages in those systems, the flow rates (or SCP production rates) are limited by that rate above which there begins to occur a washout of the microbial seed material. Very simply stated, washout refers to a situation where, because of high flow rates of nutrients through a continuous system, the loss of microbes within the reactor is greater than the gain due to cell reproduction.

Both chemostats and turbidostats are subject to wash out, thus placing an upper limit on microbe production rates. Since immobilized microbes having a high amount of biomass surface per unit volume would not be as subject to high-flow rate washout as chemostat-type systems, the value of such an immobilized system becomes readily apparent, provided cellular requirements such as nutrients, waste removal, pH, oxygen supply, etc., can be satisfied.

The value of having a high biomass surface area per unit volume is also apparent in that area of fermentation concerned with the production of secondary metabolites. For example, since secondary metabolites are generally produced in the stationary phase of microbial life cycle processes, and since the total amount of secondary metabolites produced thereby will depend on the amount of biomass surface available to release the metabolites on a continuous basis, it is clear that any system which provides a means for providing and prolonging the stationary phase of a high biomass surface will provide an ideal secondary metabolite production system. As in the case of SCP production, the retention of a large biomass surface in a given volume through which nutrients can flow at high rates also permits the rapid removal of metabolic waste products as well as useful products. Our system can also be used for primary metabolite production.

Yet another area in which the technology of this disclosure has application is the field of analytical microbiology where there are clear advantages in having available immobilized microbe composites capable of uniform delivery of a stable microbe population. The composites of this disclosure can thus be used as microbial standards which provide a reliable and convenient method of storing and handling large quantities of microbes per unit volume.

Our present disclosure is grounded on our observation that there exists a unique physical relationship between a given population of microbes which reproduce by fission and a porous support material upon which the microbes are attached such that it is possible to achieve a maximum amount of biomass surface with a minimum amount of immobilized microbe volume. To a very limited extent this observation is somewhat similar to that associated with immobilized enzyme technology wherein it has been shown that there exists a relationship between the amount of active enzyme that can be loaded on a given weight (or volume) of porous support material. See for example, U.S. Pat. No. 3,850,751, which discloses an optimum support pore size range of about 100Å to 1000Å for most immobilized enzyme systems.

It should be understood that our findings are applicable only to immobilized microbe composites in which the microbes reproduce by fission and our composites exclude those microbes which reproduce by other means (mycelial growth, budding, etc.). Hence, as used herein, the expression microbe(s) refers to those microbes (primarily bacteria) which reproduce by fission or simple division.

It should also be understood that for reasons discussed herein, the support or carrier material should be inorganic rather than organic.

An inorganic carrier material has a variety of marked advantages. The first is that microbes do not readily attack inorganic materials since their nutrient requirements are primarily focused to carbon and nitrogen containing materials. Organic carriers such as carbohydrates, proteins, etc. are readily attacked not only by the microbes but also by the extracellular enzymes that are elaborated by the organism. As the organic carrier is destroyed, the accumulation of microbes is reduced. In addition to durability, the inorganic carrier has the advantage of dimensional stability when contrasted to most organic carriers. By retaining the pore morphology under a variety of pressure and flow conditions, the microbe is protected from deformation and subsequent lysing. Again, this is an advantage in terms of biomass accumulation.

An additional advantage of an inorganic carrier is its relatively high density. Most organic materials have densities in the neighborhood of 1.0 or less while most of the inorganic materials have densities greater than 2.0 Under these circumstances, an inorganic material having an equal porosity with an organic material on a mass basis would occupy a less volume; therefore, on a volume basis the inorganic material could concentrate a greater biomass. The higher density inorganic materials have additional advantages in that lower pressure drops are experienced in plug-flow reactors and will perform better in a fluidized bed reactor since the particles will not flow to and remain at the surface, but, rather, they will continuously be agitated within the body of the solution.

A further advantage associated with the use of inorganics as microbe supports, especially according to the present disclosure, is that controlled porosity of the support can be obtained relatively simply and economically using commonly available starting materials.

Although there exists considerable information about how microbial films are formed over the surfaces of supports, less information appears to exist about the actual mechanism by which the microbes actually attach to the support. It is well known, however, that most microbes will attach to and reproduce on all but the most toxic substances. As used herein, the expression "bonded", when applied to the mode of attachment of the microbes or microbe film to the support, includes all modes of attachment whether by physical or chemical bonds or both. In some of the examples below, microbes were simply allowed to bond to the support by what appeared to be adsorptive forces. In other cases, residues of polyisocyanates or silane coupling agents were used to coat the surfaces of the support, thereby providing a possible basis for chemical bonding of the cells to the support via the coatings. The cells may also be crosslinked in place over or on the support surfaces.

The controlled population of microbes includes microbes of a given species, all being in the same general size range as well as other collections of microbes having a similarity of sizes such that at least 70% of the pores of the support have pore diameters large enough to readily admit substantially all members of the population and, for puposes of maintaining maximum usable surface area and protection against microbial washout, less than about five times the maximum dimension of the largest microbe.

The smallest and largest major dimensions of most microbes can be found in textbooks or can be determined using known techniques. Whether at least 70% of the pores of a given inorganic support have pore diameters equal to one to five times the smallest to largest given major microbe dimensions can be determined by known means such as via mercury intrusion porosimetry distribution technique. All such supports should have a high surface area. As used herein, the expression high surface area refers to a support having a surface area greater than about 0.01 m$^2$/gram. .

Our observation that there exists an opitmum pore size distribution for inorganic supports of a given population of microbes can be appreciated best by interpreting our experimental results vis-a-vis theoretical physical considerations. Although some microbes (bacteria) have a width (or smallest) dimension as large as 5μ (microns), and certain species may have a length as large as 40μ, most of the eubacteria have widths or smallest dimensions ranging in size from about 0.3 to 1.5 microns. Depending on the class of microbes involved, of course, the largest major dimension (length, instead of width), may be several times that size and that range and subject to some variation due to such factors as age, state of growth, type, nutrients, etc. In general, the smallest to largest major dimensions of the majority of fission reproducing bacteria range from about 0.5μ to about 3.0μ.

For illustrative purposes, if one were to choose a microbe the largest major dimension of which is about one micron, it can be appreciated that as that microbe undergoes fission, it increases to a maximum major dimension approaching about two microns. Thus, in the case where two of the microbes were simultaneously undergoing fission while bonded to opposite sides of the internal surfaces of a pore in a support, thereby resulting in maximum utilization of available surface area and pore volume, the pore would have to be at least $4\infty$. To permit the passage of yet another microbe through the pore from a position further down the pore to a point external to the pore, at least an additional micron of pore diameter would be needed to pass out of the pore between the immobilized microbes which were simultaneously undergoing fission at the same maximum stage (size). Therefore, while it can be appreciated that the pore diameter of the support should be at least as large as the smallest major dimension to readily admit the microbe, a higher loading of microbes or a more effective utilization of the largely internal surface area occurs when the pores are somewhat larger than the minimum size needed to readily admit microbes. We have found that the upper limit of pore size which in general permits the most effective utilization of surface area per unit volume of support is about five times the largest major dimension of the microbe bonded therein.

It should be noted that in some cases where microbe reproduction per se is not of prime concern (e.g. secondary metabolite production where a relatively constant stationary phase is desired), a moe effective untilization of internal surface area results when the bulk of the pores are closer in size to the smallest major dimension of the microbe. Thus, depending on the purpose for which the microbes are to be immobilized, it can be appeciated that, in general, the most efficient use of surface area for bonding a given population of microbes results when a majority (at least 70%) of the pores of a porous inorganic support have pore diameters ranging in sizes equal to the smallest major microbe dimension to about five times the largest major dimension. As shown in the examples below, it was found that the peak value for biomass surface accumulation was found when the support pore size was within that range. Specifically, optimal loading results were obtained when at least 70% of the pores had pore diameters about five times the smallest major microbe dimension.

The importance of controlling pore size distribution of the porous inorganic support is shown by comparing the biomass loading results obtained with separate porous supports, only one of which had a tightly controlled pore size distribution. In general, the experimental results appeared to indicate that at least about 70% of the pores should have pore diameters at least as large as the smallest major dimension of the microbe but less than about five times the largest major dimension.

In the examples below, the porous supports having a known and reasonably controlled porosity included various fritted glass materials and cordierite-like crystalline materials. The best fritted glass and cordierite supports had at least 70% of their pore sizes within the required range (.e.g. 77–100% for the fritted glass, and 76–100% for the $Al_2O_3$- cordierite). The pore size ranges in microns, (with average pore sizes in parentheses) for the support materials were as follows: fritted glasses 0.8–1.8 (1.1), 1.5–4.0 (3.1), 3.0–6.0 (4.5), 8–20 (13), 18–60 (32), 170–220 (195); cordierite-like material 2–9 (4.5), 1.5–20 (10); and 4.5–100 (18).

Because our microbe loading (biomass) determinations involved measuring the number of microbes bonded within the pores of the various porous supports, we could not use conventional plate counting techniques. Instead, the microbe counts were determined using a DuPont Biometer Model No. 760 which detemines microbe count based on the amount of ATP present in a given sample. The actual procedure used was as folows: To approximately 10–20 mg of composite add 0.5 ml of 90% DMSO (Dimethylsulfoxide) in water. Mix the suspension vigorously for 10 seconds. Allow the suspension to stand 20 minutes, then add 4.0 ml of pH 7.4 0.01M MOPS (Morpholinopropane sulfonic acid) buffer. Mix vigorously and store in ice until it is to be read in the biometer. 10μl of this solution is added to a cuvette already in the biometer which contains the luciferin-luciferase mixture. The extracted ATP reacts with the enzyme mixture to produce light which is determined quantitatively and is proportional to the amount of ATP.

The reliability of the results using the above technique is ±20%. Further information concerning the use and reliability of the Biometer measuring technique can be found in the following publication: Instruction Manual, 760 Luminescence Biometer E.I. DuPont De Nemours & Co., Instrument Products Division, Wilmington, Delaware 19898, December 1970.

Our findings and specific methods of making the composites of the present invention are illustrated in the examples below. The microbes bonded to the various supports by the indicated techniques included *Escherichia coli, Serratia marcescens, Bacillus subtilis*, and *Rhodospirillum rubrum*. Unless otherwise indicated, the support materials were in particulate form having a particle size in the range of 18–25 mesh, U.S. Standard Sieve.

EXAMPLE I

Effect of Pore Size on Bonding of Escherichia coli

Samples of *E. coli* (having major dimensions of 1 to 6μ) were bonded to the indicated supports, using sterile technique, by both simple adsorption and via silane coupling agents. The bonding by adsorption was accomplished by reacting 3 g portions of 18–25 mesh particles of the indicated supports for 3 hrs. at 22° C. with 20 ml of a suspension of the *E. coli* cells. The bonding via silane coupling agents was by reacting 2 g of 18–25 mesh particles with 20 ml of a 10% solution of γ-aminopropyltriethoxysilane in water for 2 hours at 100° C. to silanize the surfaces which were subsequently dried and reacted with 20 ml of a suspension of *E. coli* cells overnight at 22° C. to bond the microbes.

Bacteria loadings (no./gram of support) were then recorded via ATP measurement approximately 18 hrs. after composite preparation. The results are summarized in Table I. The percent of total pores having a pore diameter in the range of one times the smallest major dimension and five times the largest major dimension is shown after each average pore diameter.

TABLE I

| | (No. bacteria per gram of composite) | | |
|---|---|---|---|
| Support Material | Avg. Pore and % within 1-5× Range | Bonding Method | |
| | | Adsorption | Silane Coupling |
| Fritted Glass | 1.1 (81%) | $1.92 \times 10^9$ | $1.62 \times 10^9$ |
| " | 3.1 (100%) | $1.96 \times 10^9$ | $1.65 \times 10^9$ |
| " | 4.5 (100%) | $2.60 \times 10^9$ | $2.46 \times 10^9$ |
| " | 13 (100%) | $8.68 \times 10^8$ | $6.27 \times 10^8$ |
| " | 32 (33%) | $4.91 \times 10^8$ | $1.21 \times 10^8$ |
| " | 195 (0%) | $3.83 \times 10^8$ | $2.63 \times 10^8$ |
| Borosilicate Glass (18-25 mesh | Non-porous (0%) particles) | $1.98 \times 10^7$ | $3.25 \times 10^7$ |

Figure 1:
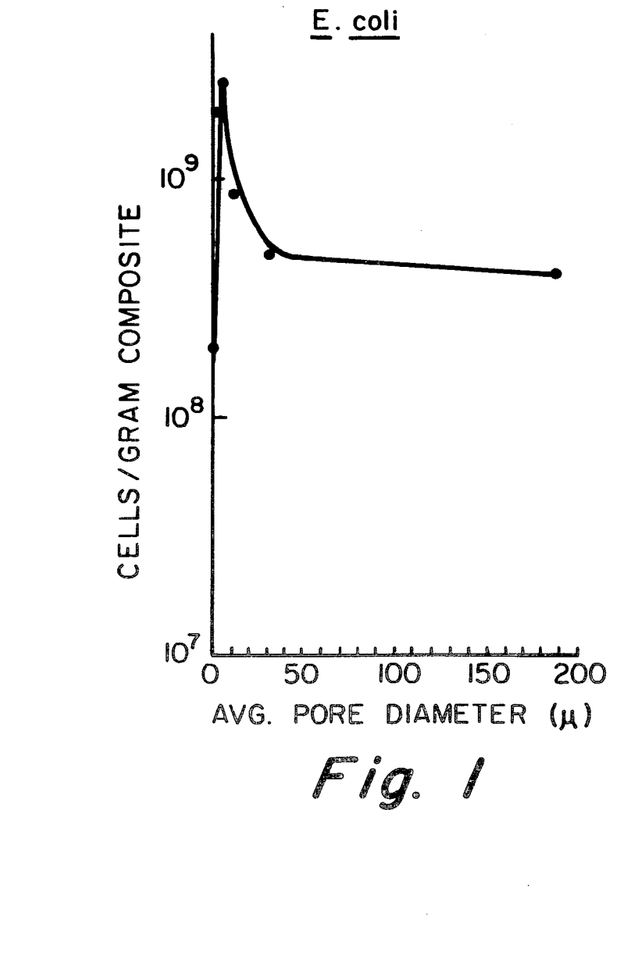
FIG. 1 is a graph illustrating the relationship between the average pore diameter of inorganic supports and the number of microbes bonded thereto.
Figure 2:
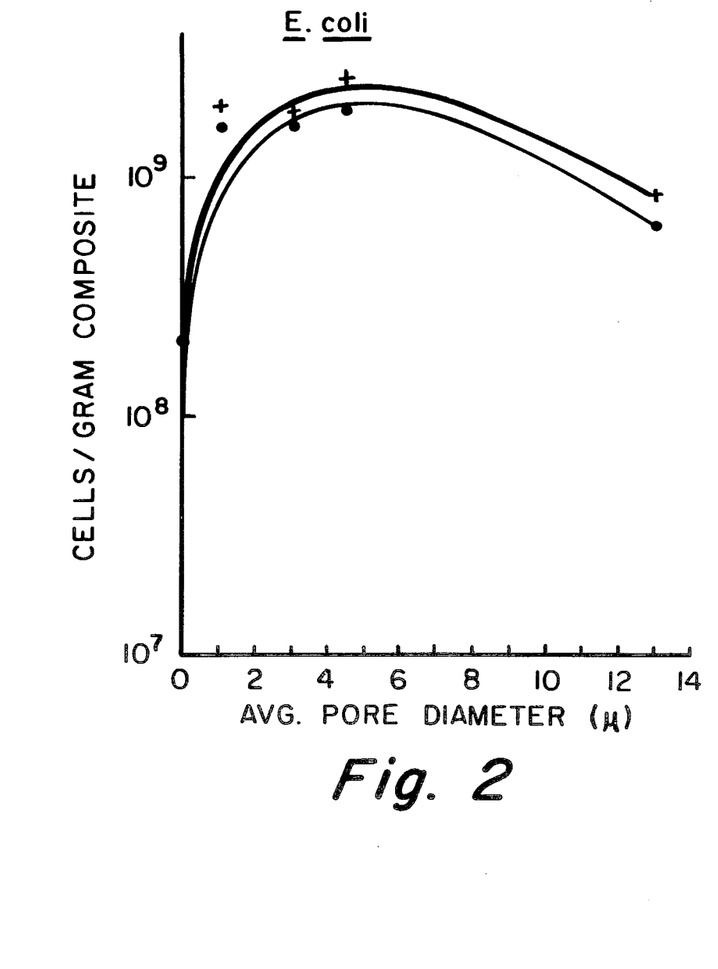
FIG. 2 represents a blown-up portion of the peak portion of FIG. 1.

From the above data, plotted in FIG. 1, it can be seen that the highest surface biomass per unit volume was obtained with the support having an average pore diameter of about 4.5 microns. See FIG. 2. It should be noted that the entire peak of FIG. 1 is included within the range of 1 times smallest major dimension and about five times the largest dimension of the *E. coli*, or about $30\mu$.

EXAMPLE II

Bonding of *Serratia Marcescens*

The bacterium *S. marcescens*, having major dimensions of 0.6 to $2.0\mu$, was bonded to similar fritted glass particles using a polyisocyanate (PAPI 901) coupling agent on the surfaces of the support. The loadings achieved by coupling and determined by biometer (ATP analysis) are recorded in Table 2 and plotted in FIG. 3. The coupling was performed as follows: 0.5 grams of carrier was used in a 50 ml microfernbach flask. Ten ml of a 0.5% solution of PAPI 901 in acetone was used as the coupling agent. After coupling to the carrier was accomplished, the PAPI 901 solution was poured off and replaced with 10 ml of a cell suspension containing $3 \times \times 10^9$ cells of *S. marcescens*/ml. The cells and carrier reacted together for three hours. The excess cells were poured off and the carrier washed three times with 0.1 N. phosphate buffer at a pH of 7.2.

TABLE 2

| Loading of S. Marcescens vs. Pore Diameters | | |
|---|---|---|
| Support Material | Average Pore Diameter ($\mu$) and % within 1-5x range | Cells per Gram |
| Fritted Glass | 1.1 (100%) | $1.64 \times 10^8$ |
| " | 3.1 (100%) | $20.2 \times 10^8$ |
| " | 4.5 (100%) | $7.5 \times 10^8$ |
| " | 13 (18%) | $5.56 \times 10^8$ |
| " | 32 (0%) | $2.93 \times 10^8$ |
| " | 195 (0%) | $0.40 \times 10^8$ |
| Borosilicate Glass | Non-porous (0%) | $1.96 \times 10^8$ |

Figure 3:
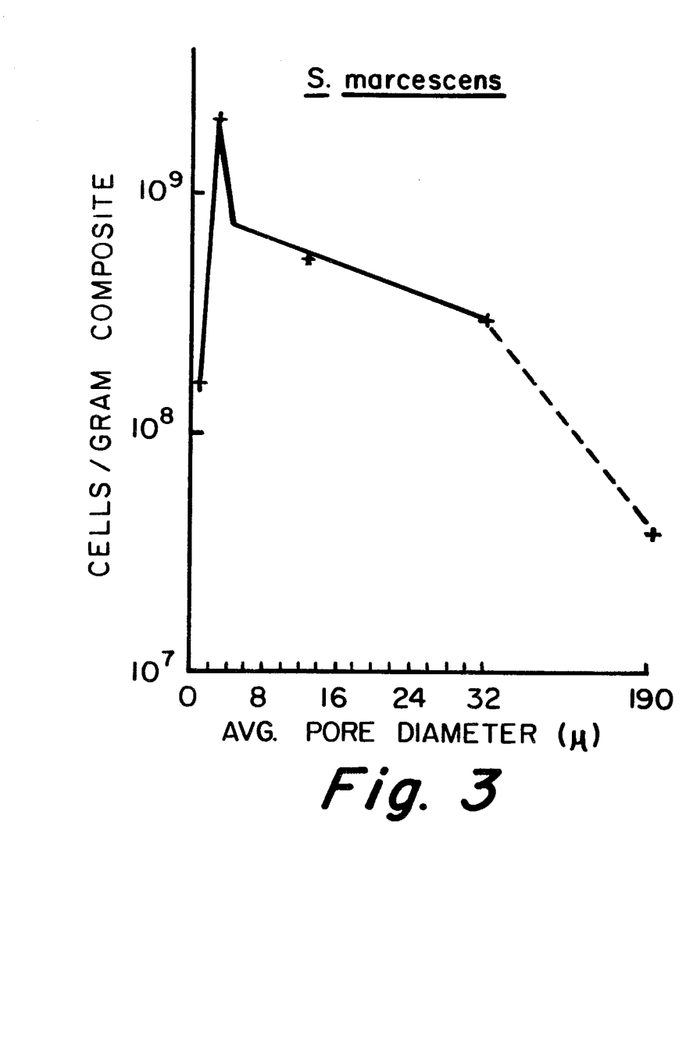
FIG. 3 is another graph illustrating the relationship between the average pore diameter of the supports and the number of microbes bonded thereto.
Figure 4:
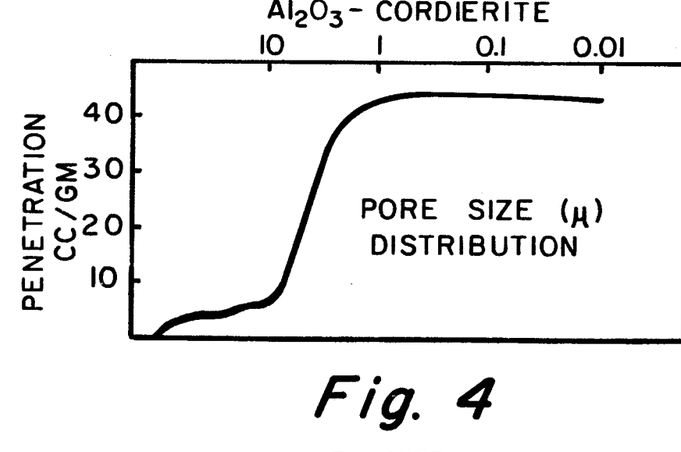
FIG. 4 represents a pore size distribution curve for a controlled porosity support.
Figure 5:
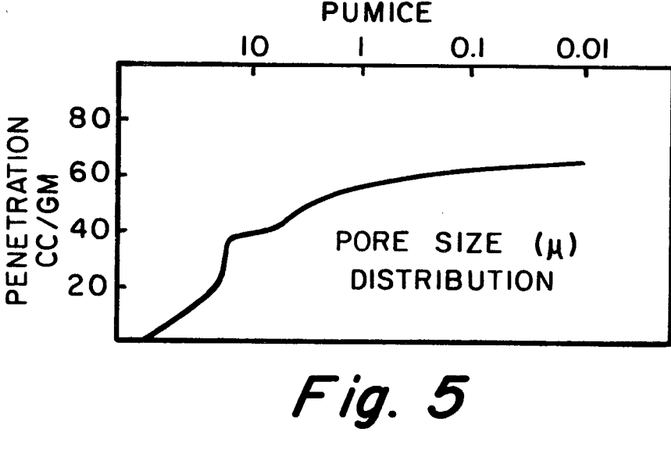
FIG. 5 represents a pore size distribution curve for a non-controlled porosity support.
Figure 6:
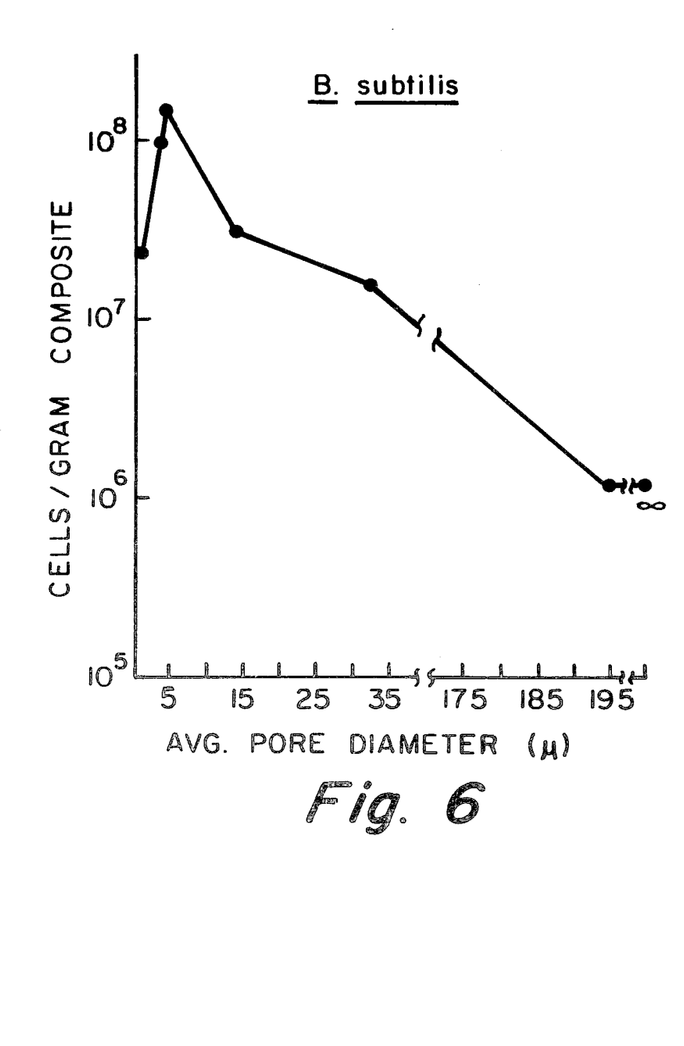
FIGS. 6 and 7 are graphs illustrating additional relationships between the average pore diameters of inorganic supports and the numbers of microbes bonded thereto.
Figure 7:
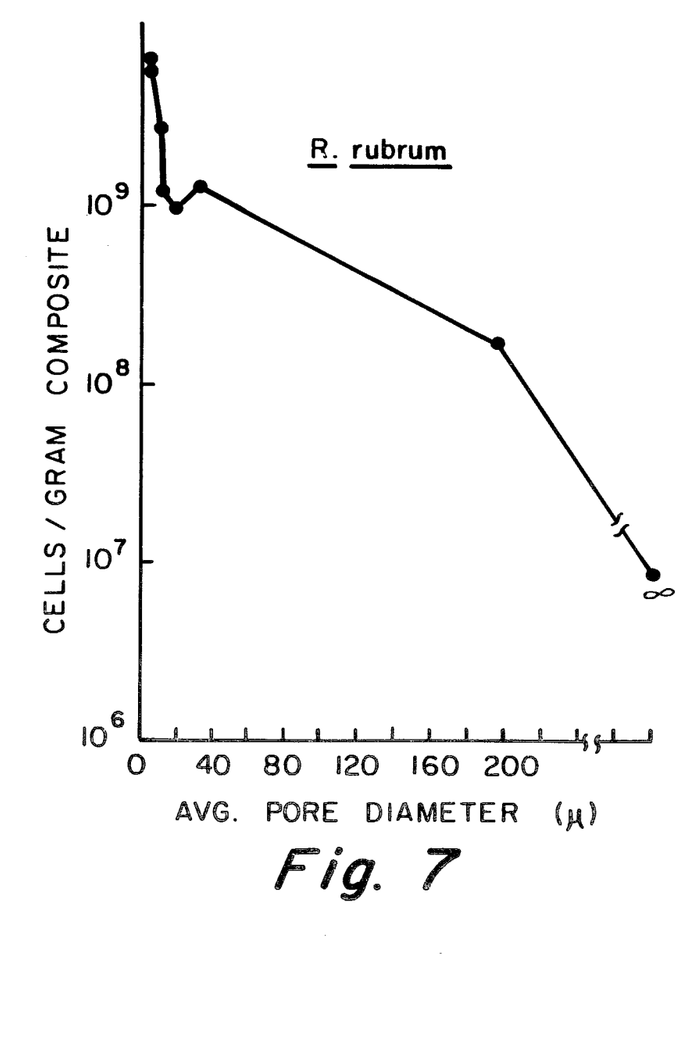

It may be readily noted in FIG. 3 that the peak value for loading is with the 3.1 micron glass and that is approximately 5 times the smallest reported value while the high biomass accumulation is just barely noted at 13 microns which is more than 5 times the largest recorded dimension reported.

EXAMPLE III

Bonding of *Bacillus Subtilis*

This experiment was performed much as the experiment using *S. marcescens* except the organism was adsorbed rather than coupled to the fritted glass carriers. Bergey's Manual, 8th Ed., p. 533, gives the size of *B subtillis* as 0.7-0.8 by $2-3\mu$. The culture as sized by microscope was approximately 1 by $3-4\mu$ with some long double cells at $7\mu$.

The carrier used was the various pore size fritted glasses which had been autoclaved "dry" and placed at 37° C. to prevent condensation.

*Bacillus subtilis* cells were grown in 1 L Brain Heart Infusion broth for 36 hours, centrifuged and the cells washed two times with sterile phosphate buffer. Ten ml of washed cell suspension was added to each flask which contained 0.5 g of carrier. After 3 hours contact time the carriers were washed 3 times and maintained at 8° C. overnight.

The number of cells on the carriers were determined by ATP measurement by the DuPont Biometer. The results, in which duplicate runs were averaged, follow:

TABLE 3

| Loading of B. Subtilis vs. Pore Diameters | | |
|---|---|---|
| Support Material | Average Bore Diameter ($\mu$) and % within 1-5x range | Average Number of Cells per g of Carrier |
| Fritted Glass | 1.1 (0%) | $2.4 \times 10^{7*}$ |
| " | 3.1 (77%) | $9.5 \times 10^7$ |
| " | 4.5 (100%) | $1.54 \times 10^8$ |
| " | 13 (100%) | $3.27 \times 10^7$ |
| " | 32 (56%) | $1.56 \times 10^{7*}$ |
| " | 195 (0%) | $1.12 \times 10^{6*}$ |
| Borosilicate Glass | Non-porous (0%) | $1.13 \times 10^{6*}$ |

*Original counts from Biometer at $10^5$, which is lower measurement limit of the Biometer The above table shows a peak in the curve between $3.1\mu$ and $13\mu$, which is within the range of 1 to 5 times the smallest to largest major dimensions of the microbe. As in the other examples, significantly less microbe loading was noted when less than about 70% of the pores were outside the range of one to five times the major dimension range of microbes.

The starred values in the table were calculated as though the $10^5$ level was real, but it could have been $10^4$ or $10^3$, etc. In any case, these numbers show some lower value below $10^7$ cells/g which emphasizes the small optimum pore size range for the *B. subtilis*.

EXAMPLE IV

Bonding of *Rhodospirillum rubrum*

The bacterium *R. rubrum*, having dimensions of $0.8\mu$ to $7-10\mu$ with some specimens having a largest size of about only $3\mu$, was bonded to a variety of supports having indicated pore sizes by simple adsorption. The bonding technique consisted of exposing or reacting a 10 ml suspension of *R. rubrum* cells/ml with 0.5 gram samples of the supports for 3 hrs. at 22° C. Cell loadings were then determined by measuring ATP concentration with the Biometer. The results are summarized below.

TABLE 4

Loading of R. rubrum vs. Pore Diameters

| Support Material | Average Pore Dia. ($\mu$) and % within 1-5x range | Cells per Gram |
|---|---|---|
| Fritted Glass | 4.5 (100%) | $6.25 \times 10^9$ |
| Cordierite 18-25 mesh | 4.5 (86%) | $5.7 \times 10^9$ |
| Cordierite 18-25 mesh | 10 (90%) | $2.7 \times 10^9$ |
| Fritted Glass | 13 (100%) | $1.21 \times 10^9$ |
| Cordierite | 18 (76%) | $9.6 \times 10^8$ |
| Fritted Glass | 32 (89%) | $1.29 \times 10^9$ |
| Fritted Glass | 195 (0%) | $1.7 \times 10^8$ |
| Borosilicate Glass | Non-porous (0%) | $9 \times 10^6$ |

*Additional Experiments*

In further work, it was found that both the bacteria *Clostridium butylicum* (3-7$\mu$), and *Flavobacterium* (1-3$\infty$) could be bonded in high quantities within the pores of the supports.

Controlled Porosity vs. No-Controlled Porosity

The importance of having a controlled pore size distribution was confirmed by comparing an inorganic support of known controlled porosity (a 20% $Al_2O_3$-80% cordierite material, having an average pore size of 2 to 9μ) with a porous inorganic (pumice) of non-controlled porosity. The bacterium *E. coli* K-12 was bonded to both porous supports via the above-described procedure using the polyisocyanate. Quantities of both composites were then placed in columns through which a nutrient solution was continuously passed.

The pumice used in this experiment was obtained commercially in the form of large chunks approximately 2–4 inches in diameter. These large pieces were broken up with a mortar and pestle and sieved to a mesh size of 18–25.

The supports (carriers) and all vessels used in the preparation of the immobilized microbes were sterilized before use. After immobilization, the carrier was washed 3–4 times with sterile phosphate buffer, pH 7.2. The slurries of immobilized cells on their individual carriers were then placed into columns used as cell generators.

The determination of microbes in the effluent medium was done by plate counting using nutrient agar as the medium.

FIGS. 4 and 5 represent the porosimetry curves for the $Al_2O_3$-cordierite support and pumice respectively. It can be seen that the pumice has a very broad range of pore sizes. The $Al_2O_3$-cordierite carrier has a rather sharply defined pore range with an average of approximately 5 microns. The surface area measurement of $Al_2O_3$-cordierite was 0.3800 $m^2/g$ while that of the pumice was 0.2100 $m^2/g$.

The volume occupied by 2 grams of the pumice was about two times that of an equal weight of the $Al_2O_3$-cordierite. Throughout the time of the experiments, there was a slight loss of column volume in the case of the pumice carrier. The loss in volume of the $Al_2O_3$-cordierite carrier was much smaller in comparison. Table 5 presents this data.

Two grams of each carrier was used for the initial immobilization. All the $Al_2O_3$-cordierite immobilized *E. coli* K12 was then placed in one of two columns, the pumice immobilized cells in another. These columns were run simultaneously, in most cases being fed from the same carboy of medium. The data in the form of plate counts is presented in Tables 4 and 5. It can be seen from examining either of the tables that in most cases the $Al_2O_3$-cordierite carrier produced a higher amount of cells than the pumice. The results from the second experiment were not as clear as those from the first experiments but still indicated that the microbial production from the controlled porosity support was greater than that from pumice.

One of the more interesting observations made during these experiments was the immediate and dramatic drop in counts after the flow rate was increased to either carrier. From an inspection of graphs based on the data, it appears that the $Al_2O_3$-cordierite support responds more dramatically than the pumice. This response may be caused by the smaller bed volume of the $Al_2O_3$-cordierite carrier.

TABLE 5

| Loss of Column Volume During Carrier Use in Microbial Generators | | | |
|---|---|---|---|
| | | Column Height in cm | |
| Experiment | Time Days | Pumice | $Al_2O_3$-cord. |
| 1 | 0 | 6.6 | 3.4 |
| 1 | 1 | 6.55 | 3.3 |
| 1 | 2 | 6.3 | 3.3 |
| 2 | 0 | 5.85 | 3.0 |
| 2 | 1 | 5.6 | 2.9 |
| 2 | 2 | 5.5 | 2.9 |

TABLE 6

| Cell Number in Effluent from E. coli Columns Using Supports of Pumice and $Al_2O_3$-Cordierite First Trial | | | | | | |
|---|---|---|---|---|---|---|
| Time Hours | Cells/ ml $\times 10^6$ | Pumice Flow Rate m/hr | Cells/ hr $\times 10^9$ | Cells/ ml $\times 10^6$ | $Al_2O_3$-Cord. Flow Rate ml/hr | Cells/ hr $\times 10^9$ |
| 0.25 | 0.05 | 50 | 0.002 | 1.0 | 50 | 0.05 |
| 1.5 | 0.03 | 50 | 0.002 | 1.0 | 50 | 0.05 |
| 3.75 | 0.02 | 50 | 0.001 | 4.0 | 50 | 0.2 |
| 4.75 | 0.02 | 106 | 0.002 | 2.0 | 95 | 0.2 |
| 20.75 | 2.0 | 106 | 0.21 | 100.0 | 95 | 9.5 |
| 21.75 | 2.0 | 253 | 0.51 | 20.0 | 240 | 4.8 |
| 22.75 | 2.0 | 253 | 0.51 | 90.0 | 240 | 21.6 |
| 23.75 | 3.0 | 253 | 0.76 | 140.0 | 240 | 34.0 |
| 24.75 | 9.0 | 253 | 2.3 | 75.0 | 240 | 18.0 |
| 25.75 | 17.0 | 253 | 4.3 | 85.0 | 240 | 204.0 |
| 25.90 | 2.0 | 490 | 1.0 | 2.5 | 502 | 1.0 |
| 26.75 | 9.0 | 490 | 4.4 | 57.0 | 502 | 27.0 |
| 27.75 | 13.0 | 490 | 6.4 | 0.6 | 502 | 0.30 |
| 28.75 | 17.0 | 490 | 8.3 | 290.0 | 502 | 146.0 |
| 45.00 | 24.0 | 490 | 11.8 | 410.0 | 502 | 206.0 |

TABLE 6-continued

Cell Number in Effluent from E. coli Columns
Using Supports of Pumice and Al$_2$O$_3$-Cordierite
First Trial

| Time Hours | Cells/ ml × 10$^6$ | Pumice Flow Rate m/hr | Cells/ hr × 10$^9$ | Cells/ ml × 10$^6$ | Al$_2$O$_3$-Cord. Flow Rate ml/hr | Cells/ hr × 10$^9$ |
|---|---|---|---|---|---|---|
| 45.75 | 11.0 | 996 | 11.0 | 460.0 | 980 | 451.0 |
| 46.75 | 28.0 | 996 | 28.0 | 750.0 | 980 | 735.0 |
| 47.75 | 27.0 | 996 | 26.0 | 210.0 | 980 | 206.0 |
| 48.75 | 12.0 | 996 | 12.0 | 590.0 | 980 | 578.0 |
| 49.25 | 28.0 | 996 | 28.0 | 90.0 | 980 | 88.0 |
| 51.25 | 30.0 | 996 | 30.0 | 120.0 | 980 | 118.0 |
| 52.50 | 29.0 | 996 | 29.0 | 120.0 | 980 | 118.0 |

TABLE 7

Cell Number in Effluent from E. coli Columns
Using Supports of Pumice and Al$_2$O$_3$-Cordierite
Second Trial

| Time Hours | Cells/ ml × 10$^6$ | Pumice Flow Rate ml/hr | Cells/ ml × 10$^9$ | Cells ml × 10$^6$ | Al$_2$O$_3$-Cord. Flow Rate ml/hr | Cells/ hr/10$^9$ |
|---|---|---|---|---|---|---|
| 0.25 | 0.37 | 22 | 0.00814 | 1.5 | 24 | 0.04 |
| 1.25 | 1.3 | 22 | 0.003 | 3.6 | 24 | 0.09 |
| 1.75 | 1.1 | 48 | 0.5 | 41.0 | 49 | 2.0 |
| 2.25 | 0.7 | 48 | 0.03 | 26.0 | 49 | 1.3 |
| 2.75 | 0.6 | 48 | 0.03 | 4.5 | 49 | 0.2 |
| 3.75 | 0.6 | 48 | 0.03 | 2.6 | 49 | 0.3 |
| 4.75 | 0.05 | 98.5 | 0.004 | 1.6 | 99.5 | 0.2 |
| 20.75 | 2.2 | 98.5 | 0.22 | 30.0 | 99.5 | 3.0 |
| 21.25 | 0.2 | 247.5 | 0.04 | 4.8 | 249 | 1.2 |
| 22.75 | 0.4 | 247.5 | 0.1 | 6.5 | 249 | 1.6 |
| 23.75 | 1.8 | 247.5 | 0.45 | 17.0 | 249 | 4.2 |
| 25.75 | 4.4 | 438 | 1.9 | 12.0 | 420 | 5.0 |
| 27.00 | 4.4 | 438 | 1.9 | 51.0 | 420 | 21.4 |
| 27.75 | 0.6 | 438 | 0.26 | 10.0 | 420 | 4.2 |
| 28.75 | 9.6 | 438 | 4.2 | 25.0 | 420 | 10.5 |
| 44.75 | 45.0 | 438 | 19.7 | 60.0 | 420 | 25.2 |
| 46.25 | 16.0 | 880 | 14.1 | 6.2 | 900 | 5.6 |
| 46.75 | 39.0 | 880 | 34.3 | 15.0 | 900 | 13.5 |
| 47.85 | 17.0 | 880 | 15.0 | 23.0 | 900 | 20.7 |
| 49.75 | 27.0 | 880 | 23.8 | 41.0 | 900 | 36.9 |
| 50.75 | 35.0 | 880 | 30.8 | 34.0 | 900 | 30.6 |
| 51.75 | 49.0 | 880 | 43.1 | 65.0 | 900 | 58.5 |
| 52.80 | 34.0 | 880 | 29.9 | 33.0 | 900 | 29.7 |

The differences in the amount of cells produced by each carrier was evident even to the eye in the first 20–24 hours of the experiments. The effluent coming from the column containing the Al$_2$O$_3$-cordierite at low flow rates (up to 500 ml/hr) was perceptively turbid while that coming from the pumice column was clear. In the first experiment, the turbidity of the effluent became approximately the same from both supports after the flow rate had reached 1 L/hr. In the second experiment, the turbidities were similar at 500 ml/hr.

From the data presented in the tables and figures, it can easily be seen that the Al$_2$O$_3$-cordierite support with its controlled pore size distribution was a more effective support for the generation of microbes than the pumice.

Since it is thought that this overall disclosure is subject to numerous variations, it is intended that the above examples should be construed as illustrative only and that the scope of the present invention should be limited only by the following claims.

We Claim:

1. An immobilized microbe composite comprising a porous, high surface area inorganic support having a controlled population of microbes bonded to the internal surfaces of the pores, the support being water-insoluble, non-toxic to the microbes, and having a controlled porosity such that at least 70% of the pores, on a pore size distribution basis, have a pore diameter at least as large as the smallest major dimension of the microbes but less than about five times the largest major dimension of the microbes.

2. The composite of claim 1 wherein the population of microbes comprises bacteria of a single species.

3. The composite of claim 1 wherein the average pore diameter is in the range of about 0.8 to 220 microns.

4. The composite of claim 1 wherein the inorganic support comprises an amorphous material.

5. The composite of claim 4 wherein the support comprises fritted glass.

6. The cmposite of claim 1 wherein the inorganic support comprises a crystalline material.

7. The composite of claim 6 wherein the support comprises a cordierite like material.

8. The composite of claim 1 wherein intermediate the support surfaces and the microbes is a coating material selected from residues of polyisocyanates and silane coupling agents.

9. A method of preparing a high surface area, low volume biomass composite comprising the step of exposing an aqueous suspension of a controlled population of microbes which reproduce by fission to a sterilized porous inorganic support material having a porosity such that at least 70% of the pores, on a pore size distribution basis, have pore diameters at least as large as the smallest major dimension of the microbes but less than about five times the largest major dimension of the microbes, the exposure being under conditions sufficient to result in the bonding of at least some of the microbes onto the internal surfaces defining the pores of the support material.

10. The method of claim 9 wherein, prior to exposure to the microbe suspension, the surfaces of the support are treated with a coating agent selected from polyisocyanates and silane coupling agents.

11. The method of claim 9 wherein the population of microbes comprises bacteria of a single species.

12. The method of claim 9 wherein the average pore diameter of the support is in the range of about 0.8 to 220 microns.

13. The method of claim 1 wherein the support comprises an amorphous material.

14. The method of claim 9 wherein the support comprises fritted glass.

15. The method of claim 9 wherein the support comprises a crystalline material.

16. The method of claim 15 wherein the support ciomprises a cordierite-like material.

* * * * *

UNITED STATES PATENT AND TRADEMARK OFFICE
CERTIFICATE OF CORRECTION

PATENT NO. : 4,153,510
DATED : May 8, 1979
INVENTOR(S) : Ralph A. Messing and Robert A. Oppermann It is certified that error appears in the above—identified patent and that said Letters Patent are hereby corrected as shown below:

Column 5, line 27, change "∞" to --µ--.

Column 5, line 48, change "moe" to --more--.

Column 7, line 49, delete "X" second occurrence--.

Column 8, line 33, change "Bore" to --Pore--.

Column 9, line 19, change "∞" to --µ--.

Column 11, line 62, after "composite" insert --, in which the microbes reproduce by fission,--.

Column 12, line 52, change "cmposite" to --composite--.

Signed and Sealed this

Fifth Day of February 1980

[SEAL]

Attest:

SIDNEY A. DIAMOND

Attesting Officer  Commissioner of Patents and Trademarks